United States Patent
Maclaren et al.

(10) Patent No.: US 6,391,651 B1
(45) Date of Patent: *May 21, 2002

(54) MATERIALS AND METHODS FOR DETECTION OF INSULIN DEPENDENT DIABETES

(75) Inventors: Noel K. Maclaren, Gainesville, FL (US); Abner L. Notkins, McLean, VA (US); Michael S. Lan, Rockville, MD (US)

(73) Assignees: The United States of America as represented by the Secretary of the Department of Health & Human Services, Washington, DC (US); University of Florida, Gainesville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/514,213

(22) Filed: Aug. 11, 1995

(51) Int. Cl.$^7$ .............................................. G01N 33/564
(52) U.S. Cl. ................... 436/506; 424/94.1; 424/185.1; 435/7.21; 435/7.91; 435/69.3; 530/352; 530/387.1; 530/399; 530/845
(58) Field of Search ............................. 435/7.21, 7.91, 435/69.3; 530/352, 387.2, 399; 424/845, 185.1, 94.1; 436/506

(56) References Cited

U.S. PATENT DOCUMENTS

| | | |
|---|---|---|
| 5,200,318 A | 4/1993 | Rabin et al. |
| 5,840,836 A | 11/1998 | Rabin .......................... 530/324 |

OTHER PUBLICATIONS

Rudinger, J. in Peptide Hormones, J. A. Parsons (Ed), University Park Press, Baltimore MD, pp. 1–7, Jun. 1976.*

Rabin, D.A. et al. (1992) "An ELISA sandwich capture assay fro recombinant fusion proteins containing glutathione–S–transferase" Journal of Immunological Methods 156:101–105.

Rabin, D.A. et al. (1992) "Cloning and Expression of IDDM–Specific Human Autoantigens" Diabetes 41:183–186.

Rabin, D.A. et al. (1992) "Islet Cell Antigen 512 is a Diabetes–Specific Islet Autoantigen Related to Protein Tyrosine Phosphatases" Journal of Immunology 152:3183–3188.

Lu, J. et al. (1994) "Isolation, Sequence and Expression of a Novel Mouse Brain cD mIA–2, and its Relatedness to Members of the Protein Tyrosine Phosphatase Family" Biochem. Biophys. Res. Commun. 204:930–936.

Atkinson, M., N.K. Maclaren (1994) "Mechanisms of Disease" New England Journal of Medicine 331: 1428–1436.

Maclaren, N.K., W.J. Riley (1985) "Thyroid, Gastric, and Adrenal Autoimmunities Associated with Insulin–Dependent Diabetes Mellitus" Diabetes Care 8(Sup. 1):34–38.

Lendrum,R., G. Walker, D.R. Gamble (1975) "Islet–Cell Antibodies in Juvenile Diabetes Mellitus of Recent Onset" The Lancet 1:880–882.

Maclaren, N.K., S.–W. Huang, J. Fogh (1975) "Antibody to Cultured Human Insulinoma Cells in Insulin–Depdnent Diabetes" The Lancet 1:997–1000.

Kaugman, D.L. et al. (1992) "Autoimmunity to Two Forms of Glutamate Decarboxylase in Insulin–dependent Diabetes Mellitus" J. Clin. Invest. 89:283–292.

Atkinson, M.A. et al. (1992) "Response of peripheral–blood monoclear cells to glutamate decarboxylase in insulin–dependent diabetes" The Lancet 339:458–459.

Harrison, L.C. et al. (1993) "Inverse relation between humoral and cellular immunity to glutamic acid decarboxylase in subjects at risk of insulin–dependent diabetes" The Lancet 341:1365–1369.

Atkonsin, M.A. et al. (1994) "Cellular Immunity to a Determinant Common to Glutamate Decarboxylase and Coxsackie Virus in Insulin–dependent Diabetes" J. Clin. Invest. 94:2125–2129.

Maclaren, N.K. (1988) "How, When, and Why to Predict IDDM" Diabetes 37(12):1591–1594.

Muir, A. et al. (1993) "Intervention Therapies for Insulin–Dependent Diabetes" Autoimmunity 16:301–310.

Atkinson, M.A. et al. (1986) "Are Insulin Autoantibodies Markers for Insulin–Dependent Diabetes Mellitus?" Diabetes 35:894–898.

Riley, W.J. et al. (1990) "A Prospective Study of the Development of Diabetes in RElatives of Patients with Insulin–Dependent Diabetes" New England Journal of Medicine 323:1167–1172.

Atkinson, M.A., N.K. Maclaren (1993) "Islet Cell Autoantigens in Insulin–dependent Diabetes" J. Clin. Invest. 92:1608–1616.

Genovese, S. et al. (1992) "Distinct cytoplasmic islet cell antibodies with different risks for Type 1 (insulin–dependent) diabetes mellitus" Diabetologia 35:385–388.

Atkinson, M.A. et al. (1993) "Islet Cell Cytoplasmic Autoantibody Reactivity to Glutamate Decarboxylase in Insulin–dependent Diabetes" J. Clin. Invest. 91:350–356.

Schatz, D. et al. (1994) "Islet Cell Antibodies Predict Insulin–dependent Diabetes in United States School Age Childredn as Powerfully as in Unaffected Relatives" J. Clin. Invest. 93:2403–2407.

(List continued on next page.)

*Primary Examiner*—Patrick J. Nolan
(74) *Attorney, Agent, or Firm*—Needle & Rosenberg, P.C.

(57) ABSTRACT

The method and compositions of this invention provide an effective and reliable substitute for the currently employed ICA assay for diabetes. By providing a method for detecting autoantibodies to both $GAD_{65}$ and IA-2 auto-antigens, the method provides a chemical assay which has improved reliability. In addition, these antigens may be employed in therapeutic regimens aimed at achieving immune tolerance and therefore amelioration of the clinical condition.

11 Claims, No Drawings-

OTHER PUBLICATIONS

Krischer, J.P. et al. (1993) "Insulin and Islet Cell Autoantibodies as Time–Dependent Covariates in the Development of Insulin–Dependent Diabetes: A Prospective Study in Relatives" Journal of Clinical Endocrinology and Metabolism 77(3):743–749.

Schott, M. et al. (1994) "$GAD_{65}$ Autoantibodies Increase the Predictability but not the Sensitivity of Islet Cell and Insulin Autoantibodies for Developing Insulin Dependent Diabetes Mellitus" Journal of Autoimmunity 7:865–872.

Payton, M.A. et al. (1995) "Relationship of the 37,000– and 40,000–$M_r$ Tryptic Fragments of Islet Antigens in Insulin–dependent Diabetes to the Protein Tyrosine Phosphatase–like Moleculae IA–2 (ICA512)" J. Clin. Invest. 96:1506–1511.

Lan, M.S. et al. (1994) "Molecular Cloning and Identification of a Receptor–Type Protein Tyrosine Phsophatase, IA–2, from Human Insulinoma" DNA and Cell Biology 13(5):505–514.

Baekkeskov, B. et al. (1990) "Identification of the 64F autoantigen in insulin–dependent diabetes as the GABA–synthesizing enzyme glutamic acid decarboxylase" Nature 347:151–156.

Maron, R. et al. (1983) "Autoantibodies to the insulin receptor in juvenile onset insulin–dependent diabetes" Nature 303:817–818.

Palmer, J.P. et al. (1983) "Insulin Antibodies in Insulin–Dependent Diabetics Before Insulin Treatment" Science 222:1337–1339.

Atkinson, M.A., N.K. Maclaren (1988) "Autoantibodies in Nonobese Diabetic Mice Immunoprecipitate 64,000–$M_r$ Islet Antigen" Diabetes 37(11):1587–1590.

Atkinson, M.A., N.K. Maclaren (1990) "What Causes Diabetes?" Scientific American 262(7):62–71.

Baekkeskov, S. et al. (1982) "Autoantibodies in newly diagnosed diabetic children immunoprecipitate human pancreatic islet cell proteins" Nature 298:167–169.

ATkinson, M.A. et al. (1990) "64,000 $M_2$ autoantibodies as predictors of insulin–dependent diabetes" The Lancet 335:1357–1360.

Baekkeskov, S. et al. (1982) "Antuantibodies to a 64–Kilodalton Islet Cell Protein Precede the Onset of Spontaneous Diabetes in the BB Rat" Science 224:1348–1350.

* cited by examiner

SEQUENCE LISTING

<160> NUMBER OF SEQ ID NOS: 3

<210> SEQ ID NO 1
<211> LENGTH: 3613
<212> TYPE: DNA
<213> ORGANISM: Artificial Sequence
<220> FEATURE:
<223> OTHER INFORMATION: Description of Artificial Sequence: /Note = synthetic construct
<221> NAME/KEY: CDS
<222> LOCATION: (74)...(3010)

<400> SEQUENCE: 1

```
cagcccctct ggcaggctcc cgccagcgtc gctgcggctc cggcccggga gcgagcgccc            60
ggagctcgga aag atg cgg cgc ccg cgg cgg cct ggg ggt ctc ggg gga              109
            Met Arg Arg Pro Arg Arg Pro Gly Gly Leu Gly Gly
              1               5                  10 tcc ggg ggt ctc cgg ctg ctc ctc tgc ctc ctg ctg agc agc cgc                 157
Ser Gly Gly Leu Arg Leu Leu Leu Cys Leu Leu Leu Ser Ser Arg
        15                  20                  25 ccg ggg ggc tgc agc gcc gtt agt gcc cac ggc tgt cta ttt gac cgc             205
Pro Gly Gly Cys Ser Ala Val Ser Ala His Gly Cys Leu Phe Asp Arg
 30                  35                  40 agg ctc tgc tct cac ctg gaa gtc tgt att cag gat ggc ttg ttt ggg             253
Arg Leu Cys Ser His Leu Glu Val Cys Ile Gln Asp Gly Leu Phe Gly
 45                  50                  55                  60 cag tgc cag gtg gga gtg ggg cag gcc cgg ccc ctt ttg caa gtc acc             301
Gln Cys Gln Val Gly Val Gly Gln Ala Arg Pro Leu Leu Gln Val Thr
            65                  70                  75 tcc cca gtt ctc caa cgc tta caa ggt gtg ctc cga caa ctc atg tcc             349
Ser Pro Val Leu Gln Arg Leu Gln Gly Val Leu Arg Gln Leu Met Ser
        80                  85                  90 caa gga ttg tcc tgg cac gat gac ctc acc cag tat gtg atc tct cag             397
Gln Gly Leu Ser Trp His Asp Asp Leu Thr Gln Tyr Val Ile Ser Gln
        95                  100                 105 gag atg gag cgc atc ccc agg ctt cgc ccc cca gag ccc cgt cca agg             445
Glu Met Glu Arg Ile Pro Arg Leu Arg Pro Pro Glu Pro Arg Pro Arg
    110                 115                 120 gac agg tct ggc ttg gca ccc aag aga cct ggt cct gct gga gag ctg             493
Asp Arg Ser Gly Leu Ala Pro Lys Arg Pro Gly Pro Ala Gly Glu Leu
125                 130                 135                 140 ctt tta cag gac atc ccc act ggc tcc gcc cct gct gcc cag cat cgg             541
Leu Leu Gln Asp Ile Pro Thr Gly Ser Ala Pro Ala Ala Gln His Arg
                145                 150                 155 ctt cca caa cca cca gtg ggc aaa ggt gga gct ggg gcc agc tcc tct             589
Leu Pro Gln Pro Pro Val Gly Lys Gly Gly Ala Gly Ala Ser Ser Ser
            160                 165                 170 ctg tcc cct ctg cag gct gag ctg ctc ccg cct ctc ttg gag cac ctg             637
Leu Ser Pro Leu Gln Ala Glu Leu Leu Pro Pro Leu Leu Glu His Leu
        175                 180                 185 ctg ctg ccc cca cag cct ccc cac cct tca ctg agt tac gaa cct gcc             685
Leu Leu Pro Pro Gln Pro Pro His Pro Ser Leu Ser Tyr Glu Pro Ala
    190                 195                 200 ttg ctg cag ccc tac ctg ttc cac cag ttt ggc tcc cgt gat ggc tcc             733
Leu Leu Gln Pro Tyr Leu Phe His Gln Phe Gly Ser Arg Asp Gly Ser
205                 210                 215                 220 agg gtc tca gag ggc tcc cca ggg atg gtc agt gtc ggc ccc ctg ccc             781
Arg Val Ser Glu Gly Ser Pro Gly Met Val Ser Val Gly Pro Leu Pro
                225                 230                 235
```

```
aag gct gaa gcc cct gcc ctc ttc agc aga act gcc tcc aag ggc ata        829
Lys Ala Glu Ala Pro Ala Leu Phe Ser Arg Thr Ala Ser Lys Gly Ile
        240                 245                 250 ttt ggg gac cac cct ggc cac tcc tac ggg gac ctt cca ggg cct tca        877
Phe Gly Asp His Pro Gly His Ser Tyr Gly Asp Leu Pro Gly Pro Ser
        255                 260                 265 cct gcc cag ctt ttt caa gac tct ggg ctg ctc tat ctg gcc cag gag        925
Pro Ala Gln Leu Phe Gln Asp Ser Gly Leu Leu Tyr Leu Ala Gln Glu
        270                 275                 280 ttg cca gca ccc agc agg gcc agg gtg cca agg ctg cca gag caa ggg        973
Leu Pro Ala Pro Ser Arg Ala Arg Val Pro Arg Leu Pro Glu Gln Gly
285                 290                 295                 300 agc agc agc cgg gca gag gac tcc cca gag ggc tat gag aag gaa gga       1021
Ser Ser Ser Arg Ala Glu Asp Ser Pro Glu Gly Tyr Glu Lys Glu Gly
                305                 310                 315 cta ggg gat cgt gga gag aag cct gct tcc cca gct gtg cag cca gat       1069
Leu Gly Asp Arg Gly Glu Lys Pro Ala Ser Pro Ala Val Gln Pro Asp
            320                 325                 330 gcg gct ctg cag agg ctg gcc gct gtg ctg gcg ggc tat ggg gta gag       1117
Ala Ala Leu Gln Arg Leu Ala Ala Val Leu Ala Gly Tyr Gly Val Glu
        335                 340                 345 ctg cgt cag ctg acc cct gag cag ctc tcc aca ctc ctg acc ctg ctg       1165
Leu Arg Gln Leu Thr Pro Glu Gln Leu Ser Thr Leu Leu Thr Leu Leu
    350                 355                 360 cag cta ctg ccc aag ggt gca gga aga aat ccg gga ggg gtt gta aat       1213
Gln Leu Leu Pro Lys Gly Ala Gly Arg Asn Pro Gly Gly Val Val Asn
365                 370                 375                 380 gtt gga gct gat atc aag aaa aca atg gag ggg ccg gtg gag ggc aga       1261
Val Gly Ala Asp Ile Lys Lys Thr Met Glu Gly Pro Val Glu Gly Arg
                385                 390                 395 gac aca gca gag ctt cca gcc cgc aca tcc ccc atg cct gga cac ccc       1309
Asp Thr Ala Glu Leu Pro Ala Arg Thr Ser Pro Met Pro Gly His Pro
            400                 405                 410 act gcc agc cct acc tcc agt gaa gtc cag cag gtg cca agc cct gtc       1357
Thr Ala Ser Pro Thr Ser Ser Glu Val Gln Gln Val Pro Ser Pro Val
        415                 420                 425 tcc tct gag cct ccc aaa gct gcc aga ccc cct gtg aca cct gtc ctg       1405
Ser Ser Glu Pro Pro Lys Ala Ala Arg Pro Pro Val Thr Pro Val Leu
    430                 435                 440 cta gag aag aaa agc cca ctg ggc cag agc cag ccc acg gtg gca gga       1453
Leu Glu Lys Lys Ser Pro Leu Gly Gln Ser Gln Pro Thr Val Ala Gly
445                 450                 455                 460 cag ccc tca gcc cgc cca gca gca gag gaa tat ggc tac atc gtc act       1501
Gln Pro Ser Ala Arg Pro Ala Ala Glu Glu Tyr Gly Tyr Ile Val Thr
                465                 470                 475 gat cag aag ccc ctg agc ctg gct gca gga gtg aag ctg ctg gag atc       1549
Asp Gln Lys Pro Leu Ser Leu Ala Ala Gly Val Lys Leu Leu Glu Ile
            480                 485                 490 ctg gct gag cat gtg cac atg tcc tca ggc agc ttc atc aac atc agt       1597
Leu Ala Glu His Val His Met Ser Ser Gly Ser Phe Ile Asn Ile Ser
        495                 500                 505 gtg gtg gga cca gcc ctc acc ttc cgc atc cgg cac aat gag cag aac       1645
Val Val Gly Pro Ala Leu Thr Phe Arg Ile Arg His Asn Glu Gln Asn
    510                 515                 520 ctg tct ttg gct gat gtg acc caa caa gca ggg ctg gtg aag tct gaa       1693
Leu Ser Leu Ala Asp Val Thr Gln Gln Ala Gly Leu Val Lys Ser Glu
525                 530                 535                 540 ctg gaa gca cag aca ggg ctc caa atc ttg cag aca gga gtg gga cag       1741
Leu Glu Ala Gln Thr Gly Leu Gln Ile Leu Gln Thr Gly Val Gly Gln
                545                 550                 555
```

-continued

| | |
|---|---|
| agg gag gag gca gct gca gtc ctt ccc caa act gcg cac agc acc tca<br>Arg Glu Glu Ala Ala Ala Val Leu Pro Gln Thr Ala His Ser Thr Ser<br>560                         565                   570 | 1789 |
| ccc atg cgc tca gtg ctg ctc act ctg gtg gcc ctg gca ggt gtg gct<br>Pro Met Arg Ser Val Leu Leu Thr Leu Val Ala Leu Ala Gly Val Ala<br>575                      580                   585 | 1837 |
| ggg ctg ctg gtg gct ctg gct gtg gct ctg tgt gtg cgg cag cat gcg<br>Gly Leu Leu Val Ala Leu Ala Val Ala Leu Cys Val Arg Gln His Ala<br>590                       595                 600 | 1885 |
| cgg cag caa gac aag gag cgc ctg gca gcc ctg ggg cct gag ggg gcc<br>Arg Gln Gln Asp Lys Glu Arg Leu Ala Ala Leu Gly Pro Glu Gly Ala<br>605                    610                615              620 | 1933 |
| cat ggt gac act acc ttt gag tac cag gac ctg tgc cgc cag cac atg<br>His Gly Asp Thr Thr Phe Glu Tyr Gln Asp Leu Cys Arg Gln His Met<br>625                      630                635 | 1981 |
| gcc acg aag tcc ttg ttc aac cgg gca gag ggt cca ccg gag cct tca<br>Ala Thr Lys Ser Leu Phe Asn Arg Ala Glu Gly Pro Pro Glu Pro Ser<br>640                   645                650 | 2029 |
| cgg gtg agc agt gtg tcc tcc cag ttc agc gac gca gcc cag gcc agc<br>Arg Val Ser Ser Val Ser Ser Gln Phe Ser Asp Ala Ala Gln Ala Ser<br>655                    660                665 | 2077 |
| ccc agc tcc cac agc agc acc ccg tcc tgg tgc gag gag ccg gcc caa<br>Pro Ser Ser His Ser Ser Thr Pro Ser Trp Cys Glu Glu Pro Ala Gln<br>670                   675                680 | 2125 |
| gcc aac atg gac atc tcc acg gga cac atg att ctg gca tac atg gag<br>Ala Asn Met Asp Ile Ser Thr Gly His Met Ile Leu Ala Tyr Met Glu<br>685                    690                695              700 | 2173 |
| gat cac ctg cgg aac cgg gac cgc ctt gcc aag gag tgg cag gcc ctc<br>Asp His Leu Arg Asn Arg Asp Arg Leu Ala Lys Glu Trp Gln Ala Leu<br>705                    710                715 | 2221 |
| tgt gcc tac caa gca gag cca aac acc tgt gcc acc gcg cag ggg gag<br>Cys Ala Tyr Gln Ala Glu Pro Asn Thr Cys Ala Thr Ala Gln Gly Glu<br>720                   725                730 | 2269 |
| ggc aac atc aaa aag aac cgg cat cct gac ttc ctg ccc tat gac cat<br>Gly Asn Ile Lys Lys Asn Arg His Pro Asp Phe Leu Pro Tyr Asp His<br>735                    740                745 | 2317 |
| gcc cgc ata aaa ctg aag gtg gag agc agc cct tct cgg agc gat tac<br>Ala Arg Ile Lys Leu Lys Val Glu Ser Ser Pro Ser Arg Ser Asp Tyr<br>750                   755                760 | 2365 |
| atc aac gcc agc ccc att att gag cat gac cct cgg atg cca gcc tac<br>Ile Asn Ala Ser Pro Ile Ile Glu His Asp Pro Arg Met Pro Ala Tyr<br>765                    770                775              780 | 2413 |
| ata gcc acg cag ggc ccg ctg tcc cat acc atc gca gac ttc tgg cag<br>Ile Ala Thr Gln Gly Pro Leu Ser His Thr Ile Ala Asp Phe Trp Gln<br>785                    790                795 | 2461 |
| atg gtg tgg gag agc ggc tgc acc gtc atc gtc atg ctg acc ccg ctg<br>Met Val Trp Glu Ser Gly Cys Thr Val Ile Val Met Leu Thr Pro Leu<br>800                    805                810 | 2509 |
| gtg gag gat ggt gtc aag cag tgt gac cgc tac tgg cca gat gag ggt<br>Val Glu Asp Gly Val Lys Gln Cys Asp Arg Tyr Trp Pro Asp Glu Gly<br>815                    820                825 | 2557 |
| gcc tcc ctc tac cac gta tat gag gtg aac ctg gtg tcg gag cac atc<br>Ala Ser Leu Tyr His Val Tyr Glu Val Asn Leu Val Ser Glu His Ile<br>830                    835                840 | 2605 |
| tgg tgc gag gac ttt ctg gtg cgg agc ttc tac ctg aag aac gtg cag<br>Trp Cys Glu Asp Phe Leu Val Arg Ser Phe Tyr Leu Lys Asn Val Gln<br>845                   850                855              860 | 2653 |
| acc cag gag acg cgc acg ctc acg cag ttc cac ttc ctc agc tgg ccg<br>Thr Gln Glu Thr Arg Thr Leu Thr Gln Phe His Phe Leu Ser Trp Pro | 2701 |

-continued

```
                    865                 870                 875
gca gag ggc aca ccg gcc tcc acg cgg ccc ctg ctg gac ttc cgc agg      2749
Ala Glu Gly Thr Pro Ala Ser Thr Arg Pro Leu Leu Asp Phe Arg Arg
            880                 885                 890 aag gtg aac aag tgc tac cgg ggc cgc tcc tgc ccc atc atc gtg cac      2797
Lys Val Asn Lys Cys Tyr Arg Gly Arg Ser Cys Pro Ile Ile Val His
            895                 900                 905 tgc agt gat ggt gcg ggg agg acc ggc acc tac atc ctc atc gac atg      2845
Cys Ser Asp Gly Ala Gly Arg Thr Gly Thr Tyr Ile Leu Ile Asp Met
    910                 915                 920 gtc ctg aac cgc atg gca aaa gga gtg aag gag att gac atc gct gcc      2893
Val Leu Asn Arg Met Ala Lys Gly Val Lys Glu Ile Asp Ile Ala Ala
925                 930                 935                 940 acc ctg gag cat gtc cgt gac cag cgg cct ggc ctt gtc cgc tct aag      2941
Thr Leu Glu His Val Arg Asp Gln Arg Pro Gly Leu Val Arg Ser Lys
                945                 950                 955 gac cag ttt gaa ttt gcc ctg aca gcc gtg gcg gag gaa gtg aat gcc      2989
Asp Gln Phe Glu Phe Ala Leu Thr Ala Val Ala Glu Glu Val Asn Ala
            960                 965                 970 atc ctc aag gcc ctg ccc cag tgagaccctg ggccccttg gcgggcagcc          3040
Ile Leu Lys Ala Leu Pro Gln
            975 cagcctctgt ccctctttgc ctgtgtgagc atctctgtgt acccactcct cactgcccca    3100 ccagccacct cttgggcatg ctcagcccctt cctagaagag tcaggaaggg aaagccagaa   3160 ggggcacgcc tgcccagcct cgcatgccag agcctgggc atcccagagc ccagggcatc    3220 ccatggggt gctgcagcca ggaggagagg aaaggacatg ggtagcaatt ctacccagag    3280 ccttctcctg cctacattcc ctggcctggc tctcctgtag ctctcctggg gttctgggag    3340 ttccctgaac atctgtgtgt gtcccccatat gctccagtat ggaagaatgg ggtggagggt   3400 cgccacaccc ggctccccct gcttctcagc cccgggcctg cctctgactc acacttgggc   3460 gctctgccct ccctggcctc acgcccagcc tggtcccacc accctcccac catgcgctgc   3520 tcaacctctc tccttctggc gcaagagaac atttctagaa aaaactactt ttgtaccagt   3580 gtgaataaag ttagtgtgtt gtctgtgcag ctg                                 3613
```

<210> SEQ ID NO 2
<211> LENGTH: 979
<212> TYPE: PRT
<213> ORGANISM: Artificial Sequence
<220> FEATURE:
<223> OTHER INFORMATION: Description of Aritficial Sequence: /Note = synthetic construct

<400> SEQUENCE: 2

```
Met Arg Arg Pro Arg Pro Gly Gly Leu Gly Gly Ser Gly Gly Leu
 1               5                  10                  15

Arg Leu Leu Leu Cys Leu Leu Leu Ser Ser Arg Pro Gly Gly Cys
                20                  25                  30

Ser Ala Val Ser Ala His Gly Cys Leu Phe Asp Arg Arg Leu Cys Ser
            35                  40                  45

His Leu Glu Val Cys Ile Gln Asp Gly Leu Phe Gly Gln Cys Gln Val
    50                  55                  60

Gly Val Gly Gln Ala Arg Pro Leu Leu Gln Val Thr Ser Pro Val Leu
65                  70                  75                  80

Gln Arg Leu Gln Gly Val Leu Arg Gln Leu Met Ser Gln Gly Leu Ser
                85                  90                  95
```

```
Trp His Asp Asp Leu Thr Gln Tyr Val Ile Ser Gln Glu Met Glu Arg
            100                 105                 110

Ile Pro Arg Leu Arg Pro Pro Glu Pro Arg Pro Arg Asp Arg Ser Gly
            115                 120                 125

Leu Ala Pro Lys Arg Pro Gly Pro Ala Gly Glu Leu Leu Leu Gln Asp
            130                 135                 140

Ile Pro Thr Gly Ser Ala Pro Ala Gln His Arg Leu Pro Gln Pro
145                 150                 155                 160

Pro Val Gly Lys Gly Gly Ala Gly Ala Ser Ser Leu Ser Pro Leu
                165                 170                 175

Gln Ala Glu Leu Leu Pro Pro Leu Leu Glu His Leu Leu Pro Pro
            180                 185                 190

Gln Pro Pro His Pro Ser Leu Ser Tyr Glu Pro Ala Leu Leu Gln Pro
            195                 200                 205

Tyr Leu Phe His Gln Phe Gly Ser Arg Asp Gly Ser Arg Val Ser Glu
            210                 215                 220

Gly Ser Pro Gly Met Val Ser Val Gly Pro Leu Pro Lys Ala Glu Ala
225                 230                 235                 240

Pro Ala Leu Phe Ser Arg Thr Ala Ser Lys Gly Ile Phe Gly Asp His
            245                 250                 255

Pro Gly His Ser Tyr Gly Asp Leu Pro Gly Pro Ser Pro Ala Gln Leu
            260                 265                 270

Phe Gln Asp Ser Gly Leu Leu Tyr Leu Ala Gln Glu Leu Pro Ala Pro
            275                 280                 285

Ser Arg Ala Arg Val Pro Arg Leu Pro Glu Gln Gly Ser Ser Ser Arg
            290                 295                 300

Ala Glu Asp Ser Pro Glu Gly Tyr Glu Lys Glu Gly Leu Gly Asp Arg
305                 310                 315                 320

Gly Glu Lys Pro Ala Ser Pro Ala Val Gln Pro Asp Ala Ala Leu Gln
            325                 330                 335

Arg Leu Ala Ala Val Leu Ala Gly Tyr Gly Val Glu Leu Arg Gln Leu
            340                 345                 350

Thr Pro Glu Gln Leu Ser Thr Leu Leu Thr Leu Leu Gln Leu Leu Pro
            355                 360                 365

Lys Gly Ala Gly Arg Asn Pro Gly Gly Val Val Asn Val Gly Ala Asp
            370                 375                 380

Ile Lys Lys Thr Met Glu Gly Pro Val Glu Gly Arg Asp Thr Ala Glu
385                 390                 395                 400

Leu Pro Ala Arg Thr Ser Pro Met Pro Gly His Pro Thr Ala Ser Pro
            405                 410                 415

Thr Ser Ser Glu Val Gln Gln Val Pro Ser Pro Val Ser Ser Glu Pro
            420                 425                 430

Pro Lys Ala Ala Arg Pro Pro Val Thr Pro Val Leu Leu Glu Lys Lys
            435                 440                 445

Ser Pro Leu Gly Gln Ser Gln Pro Thr Val Ala Gly Gln Pro Ser Ala
            450                 455                 460

Arg Pro Ala Ala Glu Glu Tyr Gly Tyr Ile Val Thr Asp Gln Lys Pro
465                 470                 475                 480

Leu Ser Leu Ala Ala Gly Val Lys Leu Leu Glu Ile Leu Ala Glu His
            485                 490                 495

Val His Met Ser Ser Gly Ser Phe Ile Asn Ile Ser Val Val Gly Pro
            500                 505                 510

Ala Leu Thr Phe Arg Ile Arg His Asn Glu Gln Asn Leu Ser Leu Ala
```

-continued

```
                515                 520                 525
Asp Val Thr Gln Gln Ala Gly Leu Val Lys Ser Glu Leu Glu Ala Gln
                530                 535                 540
Thr Gly Leu Gln Ile Leu Gln Thr Gly Val Gly Gln Arg Glu Glu Ala
545                 550                 555                 560
Ala Ala Val Leu Pro Gln Thr Ala His Ser Thr Ser Pro Met Arg Ser
                565                 570                 575
Val Leu Leu Thr Leu Val Ala Leu Ala Gly Val Ala Gly Leu Leu Val
                580                 585                 590
Ala Leu Ala Val Ala Leu Cys Val Arg Gln His Ala Arg Gln Gln Asp
                595                 600                 605
Lys Glu Arg Leu Ala Ala Leu Gly Pro Glu Gly Ala His Gly Asp Thr
610                 615                 620
Thr Phe Glu Tyr Gln Asp Leu Cys Arg Gln His Met Ala Thr Lys Ser
625                 630                 635                 640
Leu Phe Asn Arg Ala Glu Gly Pro Pro Glu Pro Ser Arg Val Ser Ser
                645                 650                 655
Val Ser Ser Gln Phe Ser Asp Ala Ala Gln Ala Ser Pro Ser Ser His
                660                 665                 670
Ser Ser Thr Pro Ser Trp Cys Glu Glu Pro Ala Gln Ala Asn Met Asp
                675                 680                 685
Ile Ser Thr Gly His Met Ile Leu Ala Tyr Met Glu Asp His Leu Arg
                690                 695                 700
Asn Arg Asp Arg Leu Ala Lys Glu Trp Gln Ala Leu Cys Ala Tyr Gln
705                 710                 715                 720
Ala Glu Pro Asn Thr Cys Ala Thr Ala Gln Gly Glu Gly Asn Ile Lys
                725                 730                 735
Lys Asn Arg His Pro Asp Phe Leu Pro Tyr Asp His Ala Arg Ile Lys
                740                 745                 750
Leu Lys Val Glu Ser Ser Pro Ser Arg Ser Asp Tyr Ile Asn Ala Ser
                755                 760                 765
Pro Ile Ile Glu His Asp Pro Arg Met Pro Ala Tyr Ile Ala Thr Gln
770                 775                 780
Gly Pro Leu Ser His Thr Ile Ala Asp Phe Trp Gln Met Val Trp Glu
785                 790                 795                 800
Ser Gly Cys Thr Val Ile Val Met Leu Thr Pro Leu Val Glu Asp Gly
                805                 810                 815
Val Lys Gln Cys Asp Arg Tyr Trp Pro Asp Glu Gly Ala Ser Leu Tyr
                820                 825                 830
His Val Tyr Glu Val Asn Leu Val Ser Glu His Ile Trp Cys Glu Asp
                835                 840                 845
Phe Leu Val Arg Ser Phe Tyr Leu Lys Asn Val Gln Thr Gln Glu Thr
                850                 855                 860
Arg Thr Leu Thr Gln Phe His Phe Leu Ser Trp Pro Ala Glu Gly Thr
865                 870                 875                 880
Pro Ala Ser Thr Arg Pro Leu Leu Asp Phe Arg Arg Lys Val Asn Lys
                885                 890                 895
Cys Tyr Arg Gly Arg Ser Cys Pro Ile Ile Val His Cys Ser Asp Gly
                900                 905                 910
Ala Gly Arg Thr Gly Thr Tyr Ile Leu Ile Asp Met Val Leu Asn Arg
                915                 920                 925
Met Ala Lys Gly Val Lys Glu Ile Asp Ile Ala Ala Thr Leu Glu His
930                 935                 940
```

```
Val Arg Asp Gln Arg Pro Gly Leu Val Arg Ser Lys Asp Gln Phe Glu
945                 950                 955                 960

Phe Ala Leu Thr Ala Val Ala Glu Glu Val Asn Ala Ile Leu Lys Ala
                965                 970                 975

Leu Pro Gln

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence:  /Note =
      synthetic construct

<400> SEQUENCE: 3
gccgccacca tgg                                                            13
```

MATERIALS AND METHODS FOR DETECTION OF INSULIN DEPENDENT DIABETES

This invention was made with government support under National Institutes of Health grant numbers R01 HD 19469, P01 DK39079 and GCRC M01 RR00082. The government has certain rights in the invention.

BACKGROUND OF THE INVENTION

Diabetes is a term that refers to a collection of diseases resulting in disordered energy metabolism and varying degrees of blood glucose elevations or hyperglycemia. One of the best characterized forms of the disease is that resulting in immunologically mediated destruction of the insulin secreting pancreatic beta cells. This severe form of the disease is termed Insulin Dependent Diabetes (IDD) since it is associated with progressive insulin deficiency and coincident symptoms such as weight loss, glycosuria and polyuria, and increased thirst or polydipsia. Other terms for this form of diabetes are Type 1 Diabetes (cf. Type 2 Diabetes which results from an inherent resistance to insulin action); Ketosis Prone Diabetes because there is abnormal generation of ketone bodies as a result of excessive breakdown of body fats due to the severe insulin deficiency, or Juvenile Diabetes, since virtually all diabetes that appears in childhood and adolescence is of this type (see Atkinson and Maclaren, N Engl J Med 1994:331:1428–1436).

Diabetes is a major public health problem, especially in Western countries. The incidence rates vary greatly worldwide, from as high as 40 per 100,000 persons in Finland to as low as 1–2 per 100,000 among Japanese, with the US in between. The peak incidence is during the pubertal years associated with increasing bodily demands for insulin associated with muscle growth. The prevalence rates in the US population under age 20 years is 0.25% and it approaches 0.4% over a lifetime, albeit an estimated 10–20% of patients with Non Insulin Dependent Diabetes (NIDD) or Type 2 or Maturity Onset Diabetes also have, in reality, slowly progressive IDD. Thus, it is estimated that there should be at least 1 million Americans affected by IDD.

Diabetes results in progressive damage to the blood vessels of the body, to a degree that depends upon the severity of hyperglycemia and its duration. The incident mortality rate for IDD has been calculated to be 7 fold higher than for age matched non diabetic controls. Whereas the decade long Diabetes Control and Complications Trial (DCCI) concluded in 1994 by the National Institutes of Health in the US showed that meticulous insulin replacement therapy would slow the appearance of damaged arteries, it was not able to prevent this since blood glucose levels were never kept within normal limits. Ocular complications of diabetes are the leading cause of new blindness in persons of 20–74 years of age. The risk of lower extremity amputation is 15 fold higher in those with diabetes, while more than half of the approximately 125,000 persons undergoing lower limb amputation do so as a direct consequence of diabetes. Approximately 40% of persons undergoing renal transplantations have kidney failure because of their diabetes, and the proportion due to diabetes continues to rise each year. Women with diabetes produce newborn infants with a 7% newborn mortality rate, albeit this outcome can be greatly improved with tight glycemic control during the gestation period. Other complications of diabetes include increased heart disease and stroke, loss of nerve cells or neurones innervating the limbs and intestine, impotence and infertility, cataract formation in the lens of the eyes, increased periodontal disease, and predisposition to infectious diseases especially from bacteria and yeast. Of all patients with diabetes, those with IDD have a disproportionate share of these complications because of its severity and usual early age of onset In the US, the direct health care costs attributable to diabetes in 1994 have been estimated to exceed $120 billion. Thus it is important that the pathogenesis of IDD be understood and strategies be developed to prevent it as a fully expressed clinical disease.

Patients with IDD are unusually prone to other diseases that have become recognized to have autoimmune origins. These diseases include thyroiditis or Hashimoto disease, Graves disease, Addison disease, atrophic gastritis and pernicious anemia, celiac disease and vitiligo (Maclaren, Diabetes Care 1985:8 suppl:3438). Evidence that IDD itself has an autoimmune nature began with histological studies of patients that succumbed at diagnosis which indicated that the islets were infiltrated with a chronic inflammatory (lymphocytic) infiltrate termed insulitis. This was supported in the early 1970's by reports of islet cell autoantibodies reactive to antigens within the cytoplasm (ICA) (Lendrum et al. Lancet 1975:1:880–882) or confined to the islet cell surfaces (ICSA) (Maclaren et al. Lancet 1975:1:977–1000) as detectable by indirect immunofluorescence. Later it was recognized that many patients also develop autoantibes to insulin (IAA) before their diagnosis (Pahner et al., Science 1983:222:1337–1339) as well as to insulin receptors (Maron et al., Nature 1983:303:817–818). Autoantibodies were also reported to an islet cell protein composition of 64,000 M.Wt. in man (Baekkeskov et al., Nature 1982:298:167–169), in the Biobreeding (BB) rat model (Baekkeskov et al., Science 1984:224:1348–1350) and in the Non Obese Diabetic (NOD) mouse model (Atkinson and Maclaren, Diabetes 1988:37:1587–1590). This 64 KDa antigen has subsequently been reported to be the lower molecular weight isoform of glutamic acid decarboxylase ($GAD_{65}$) (Baekkeskov et al., Nature 1990:347:151–156) (Kauffman et al., J Clin Invest 1992: 283–292). GAD is an enzyme that converts glutamate into the membrane stabilizing neurotransiitter called gamma amino butyric acid or GABA. In addition to autoantibodies to GAD, peripheral blood mononuclear cells were shown to be autoreactive in patients developing IDD (Atkinson and Maclaren et al., Lancet 1992:339: 458–459, and Harrison et al. Lancet 1993:341: 1365–1369). Indeed a leading possible cause for IDD is that immunity to enteroviral proteins (developed through infection by Coxsackie or closely related viruses) that have structural homologies to GAD, may in the genetically predisposed individual, trigger an autoimmune response to islet cells because of this molecular mimicry (Atkinson and Maclaren, Scientific American 1990:262:61–71; Kauffman et al. J Clin Invest 1992:89: 283–292; Atkinson, Maclaren et al., J Clin Invest 1994:94: 2125–2129).

Since the above immunological markers predate the clinical onset of IDD often by many years, their possible value in disease prediction became increasingly realized (Maclaren, Diabetes 1988:37:1591–1594), permitting in turn options for therapeutically induced delays in diabetes onset to be considered (Muir and Maclaren, J Autoimmunity 1993:16:301–310). Indeed by 1994, multicenter trials attempting to prevent IDD through prophylactic parenteral insulin or oral insulin therapies had been initiated in the US (the DPT-1 trial), as well as in Europe using prophylactic nicotinamide (the ENDIT trial). Among relatives, the appearance of LAA was shown to predate onset of IDD (Atkinson and Maclaren, Diabetes 1985:35: 894–898) while ICA proved to be valuable to the prediction of IDD in relatives (Riley, Maclaren et al., N Engl J Med 1990:323: 1167–1172) as well as in the general population (Schatz, Maclaren et al., J Clin Invest 1994:93: 2403–2407), as modifiable on the basis of coincident IAA (Krischer, Maclaren et al., J Clin Endo Metab 1993:77: 743–749). While not ideal the predictability of IDD based upon the ICA test provided the basis for the DPT-1 and ENDIT trials mentioned above. Furthermore, autoantibodies to the 64KDa islet cell protein also proved to have utility in IDD prediction (Atkinson, Maclaren et al., Lancet 1990:335: 1357–1360), as eventually realized by the chemical assay for autoantibodies to $GAD_{65}$. (Schott, Maclaren et al., J Autoimmunity 1994:7:865–872). These studies made it important to resolve the nature of all of the islet cell autoantigens involved in the pathogenesis of IDD (Atkinson and Maclaren, J Clin Invest 1993;92:1608–1616). Whereas ICA, as determined by indirect immunofluorescence of human cryocut pancreatic sections, was likely to represent multiple autoantigens (Genovese et al., Diabetologia 1992:35:385–388), GAD soon proved to be one of these (Atkinson, Maclaren et al. J Clin Invest 1993:91:350–356). Insulin, however, was not a component of ICA unless the pancreatic sections were first chemically "fixed" before being used as tissue substrate.

Recently, a 3.6-kb cDNA with a 2,937-bp open reading frame was isolated from a human insulinoma subtraction library (ISL-153) as described by Lan et al. (1994, DNA and Cell Biology, 13:505–514, herein incorporated by reference). The predicted amino acid sequence and in-vitro-translated product of IA-2 cDNA revealed a 979-amino acid protein with a PI value of 7.09 and a molecular mass of 105,847 daltons. The protein sequence is consistent with a signal peptide, an extracellular domain, a transmembrane domain and an intracellular domain. The extracellular domain contains an unusual cysteine-rich region following the signal peptide. The intracellular cytoplasmic domain of IA-2 possesses highly conserved regions similar to the catalytic domains in members of the protein tyrosine phosphatase (PIP) family. Northern blot analyses showed that IA-2 MRNA was expressed in five of five freshly isolated human insulinomas, rat and mouse insulinoma cell lines, and in enriched normal mouse islets. It was also found in normal human brain, pituitary, pancreas, and brain tumor cell lines, but not in a variety of other normal or tumor tissues. Based on the sequence and expression data, it appears that IA-2 is a new member of the receptor-type PTP family that is expressed in islet and brain tissues. The involvement of the molecule in beta cell autoimmunity or IDD was queried but was not disclosed or suggested in that work.

BRIEF SUMMARY OF THE INVENTION

The invention described herein concerns a novel means of accurately detecting the early stages of IDD, such that risk for the disease can be assessed. Also described are means of treating IDD and thereby preventing the occurrence of its clinical manifestations.

It has been found that autoantibodies to islet cells (ICA) can be used as important predictors of IDD. However, their predictive value in individuals found to have them is quite variable. When found in the absence of IAA, they give an overall predictability for IDD of about 1 in 4 over 5 years, but the rate of progression to IDD rises up to 2 in 3 when found together with IAA, at least in non-diabetic relatives of patients with IDD (Krischer, Maclaren et al 1994: J CGn Endo Metab 1993: 77:743–749). Among non diabetic relatives of families affected by IDD who are under the age of 10 years when ICA are discovered, ICA strongly predict IDD (Riley, Maclaren et al. N Engl J Med 1990:323:1167–1172). The instant invention is based on the component autoantibodies and autoantigens that comprise the ICA reaction, which provide differential information as to the degree of predictive power of ICA, Appearance of these component autoantbodies aids in the identification of the stage of the disease and thus in the time to clinical diagnosis. The indirect immunofluorence based ICA test is cumbersome to perform, and does not replicate as well as chemically based assays. One component of the ICA reaction is that explained by autoantibodies to $GAD_{65}$, and this latter determination has become available through immunoassays.

The instant invention identifies a second autoantibody component of the ICA reaction, which is directed to a an islet cell member of the receptor type of the tyrosine phosphatase family, termed IA-2. We identify the human IA-2 gene product as a major autoantigen of importance to IDD. We sequenced and cloned the IA2 gene, and expressed the gene product in rabbit reticulocytes, to detect the corresponding autoantibody. Detection of autoantbodies to the $GAD_{65}$ and to IA-2 antigens effectively substitutes for the cumbersome and less than completely reliable ICA assay with a reliable, chemically based assay. Further, the availability of recombinant IA-2 permits the antigen to be used alone or in combination with other antigens in a therapeutic regimen to delay the onset or progression of clinical IDD.

A further embodiment of the subject invention concerns the use of fragments of the full-length IA-2 molecule to detect antibodies to IA-2. Such fragments would, preferably, be larger than the fragment known as ICA 512 as described by Rabin et al. (Rabin et al., *Journal of Immunology* 1994:152:3183–3188).

Accordingly, it is an object of this invention to provide methods and compositions for the immune detection of insulin dependent diabetes and susceptibility to IDD.

Another object of the invention is to provide methods and compositions for the immunoprophylaxis and treatment of IDD. Other objects of the invention will become clear from the complete disclosure.

DETAILED DESCRIPTION OF THE INVENTION

The invention described here relates to the detection of antibodies to insulin antigen-2 (IA-2), alone or in combination with other antigens, as an accurate and specific early indicator of the onset of Insulin Dependent Diabetes (IDD).

IA-2 has been recently identified as a member of the transmembrane protein tyrosine phosphatase family. The complete amino acid sequence of IA-2 has been determined and the protein can be expressed as described herein in bacteria or eukaryotic cells.

Of sera from 55 diabetic patients, 45.4% reacted by ELISA with IA-2 expressed as intracellular and extracellular components in *E. coli* as compared to only 7.5% of normal controls. Analysis of newly-diagnosed (less than one year) IDD patients revealed that 50% reacted with IA-2 as did 38% of patients with longer term diabetes. Reactivity of IDD sera with glutamic acid decarboxylase ($GAD_{65}$) as compared to reactivity with IA-2 showed that 60% of $GAD_{65}$-negative IDD sera were positive for IA-2. Further experiments revealed that both rabbit antibody raised to IA-2, and human IDD sera positive for IA-2 antibody and affinity purified by passage through an IA-2 column, specifically stained cells in the pancreatic islets of Langerhans, but not surrounding acinar tissue.

One aspect of the subject invention is the discovery that IA-2 is an autoantigen in IDD and is responsible for some of the staining of islets by islet-cell autoantibody positive sera, especially those negative for reactivity to the $GAD_{65}$ antigen. These findings suggest that testing for autoantibodies to both $GAD_{65}$ and IA-2 can be used to provide a reliable method for identifying IDDM patients using chemical assays which are more reproducible than possible using the indirect immunofluorescence for ICA.

IA-2 is a 105,847 kDa transmembrane protein that belongs to the protein tyrosine phosphatase family. Immunoperoyidase staining with antibody raised against IA-2 confirms that this protein is expressed in human pancreatic islet cells. In one embodiment of the subject invention, the full-length cDNA clone of IA-2 can be expressed in a rabbit reticulocyte transcription/translation system and the recombinant radiolabelled IA-2 used as an antigen to detect autoantibodies by immunoprecipitation.

IA-2 can be expressed and isolated and used as an antigen to produce immune tolerance and immunosuppression to ameliorate or prevent IDD. The IA-2 may also be introduced into a patient with an adjuvant, such as alum or any other adjuvant accepted for introduction into people. Furthermore, the antigen can be expressed in a recombinant viral vaccine or the DNA coding for IA-2 could be introduced into an individual for expression in muscle or other cells to achieve immune tolerance and thus prevent or ameliorate IDD.

One hundred coded sera were tested by this method, 50 from patients with newly diagnosed IDD and 50 from age-matched normal controls. Sixty-six percent of the sera from patients, but none of the sera from controls, reacted with IA-2. The same diabetic sera tested for autoantibodies to glutamic acid decarboxylase ($GAD_{65}Ab$) by depletion-ELISA and to islet cells by indirect immunofluorescence showed 52% and 68% positivity, respectively. Up to 86% of the IDD patients had autoantibodies to IA-2 and/or $GAD_{65}$. Patients diagnosed with IDD before age 20 were more likely to have autoantibodies to IA-2 than patients diagnosed after age 20. Over 90% (14 of 15) of sera that were ICA-positive, but $GAD_{65}$ Ab-negative, had autoantibodies to IA-2. Absorption experiments showed that the immunofluorescence reactivity of sera containing ICA was greatly reduced by prior incubation with recombinant IA-2 or $GAD_{65}$ when the respective antibody was present. It is concluded that IA-2 is a major islet cell autoantigen in IDD pathogenesis, and is responsible, in part, for the reactivity of ICA with pancreatic islets. Tests for the detection of autoantibodies to recombinant IA-2 and $GAD_{65}$ have advantages over ICA as a predictor and identifier of patients with IDD.

Full-length IA-2 cDNA expressed in a eukaryotic expression system, can be used to create a radioimmunoassay for detecting autoantibodies to IA-2. Two thirds of our IDD patients had autoantibodies to IA-2, as compared to none of the controls. The radioimmunoassay is considerably more sensitive and specific than an ELISA test which employs the full-length of the intracellular domain of IA-2. Moreover, the radioimmunoassay used here is a liquid-phase assay and is therefore more likely to detect conformational epitopes than solid-phase ELISA. Fragments of the full-length protein can also be used.

Following are examples which illustrate procedures, for practicing the invention. These examples should not be construed as limiting. All percentages are by weight and all solvent mixture proportions are by volume unless otherwise noted.

EXAMPLE 1

Evidence That Autoantibodies to IA-2 Occur in Patients With IDD

The intracellular (aa 603–979) and extracellular (aa 129–472) domains of IA-2 were expressed as fusion proteins with glutathioine transferase (GST) from separate subclones in a pGEX bacterial expression vector. The cDNAs were verified by direct DNA sequencing, and the fusion proteins were induced by IPTG and purified by glutathione-agarose (Sigma). The fusion proteins were further processed by cleavage with human thrombin (Sigma) and the GST fusion partner removed by passage through a glutathioine-agarose alhnity column.

New Zealand rabbits were immunized against the extra and intra-mllular fragments of IA-2 to provide hyperimmune sera. An EUISA for IA-2 autoantibodies was developed as follows. Polyvinyl microtiter plates (Becton-Dickerson, Oxnard, Calif.) were coated with 0.4 µg/100 µl/well of the purified IA-2 fragments or GST expression proteins. The sera from 55 patients with IDD and 53 normal control persons were tested. Some 34% of the patients had IDD diagnosed within a year. One hundred µg of the human sera was diluted 1:50 (IC domain) or 1:100 (EC domain) in BLOTTO-Tween (10 mM Tris-HCl, pH &0; 150 mM NaCl; 5% Carnation nonfat dry milk; 0.05% Tween 20; 0.05% $NaN_3$) and reacted with the antigens. The autoantibodies were in turn detected using a 1:2000 dilution of alkale phosphatase labelled goat anti-human IgG (Southern Biotechnology Assoc. Birmingham Ala. ) in BLOITO-Tween. Polyacrylamide gel electrophoresis of the recombinant IA-2 fragments revealed bands of the predicted molecular weights, as confirmed by reactivity with the specific polyvalent rabbit antibodies, which also stained pancreatic islets. Of the patients, 21 reacted to the intracellular domain and 10 to the extracellular domain of IA-2, compared to 3 and 2 control sera respectively while 6 patients but only 1 control serum reacted to both fragments. Thus 25 patients (45.5%) had autoantibodies to the IA antigen overall, compared to only 4 controls (7.5%). Of the newly diagnosed patient group, 17 of 34 (50%) had IA-2 autoantibodies, while fewer (3&1%) had antibodies persisting beyond 1 year after diagnosis. Autoantibodies were also determined to $GAD_{65}$ produced by a baculo-viral insect cell expression system, using a depletion ELISA assay (D-ELISA). Some 20 of the patients (37.7%) were found to be negative while all of the controls were negative. Strikingly, 21 of 29 IA-2 autoantibody negative patients (72%) were found to be $GAD_{65}$ autoantibody positive. Therefore, determination of both antibodies would correctly identify considerably more of the patients than would be possible by either antibody alone.

TABLE I

Reactivity of Sera From Diabetic Patients to IA-2 in Relationship to the Presence or Absence of Autoantibodies of $GAD_{65}$

| Diabetic Patients | | IA-2 | | | |
|---|---|---|---|---|---|
| (n = 53) | | Positive* | | Negative | |
| $GAD_{65}$ | n | % | n | % | n | % |
| Negative | 20 | 37.7 | 12 | 60 | 8 | 40 |
| Positive | 33 | 62.3 | 12 | 36 | 21 | 64 |

(*)Samples with reactivity to the intracellular and/or extracellular domains of IA-2.

EXAMPLE 2

Evidence That IA-2 is a Major Autoantigen in IDD

Since IA-2 is an integral membrane protein expressed in its native state in restricted cell types in humans, the full length cDNA was next expressed in an eukaryotic rabbit reticulocyte transcription/translation system, and the recombinant protein radiolabelled with $S_{35}$ methionine was used to detect IA-2 autoantibodies by immunoprecipitation. The full length CDNA without its leader sequence was cloned into a pCRII cloning vector (Invitrogen, San Diego Calif.) with a perfect Kozak translational start sequence SEQ IS NO: 5 (GCCGCCACCATGG). One microgram of plasmid DNA was added to TNT coupled rabbit reticulocyte lysate system (Promega, Madison Wis.) in the presence of [$^{35}$S] methionine (Amersham, Arlington Heights, Ill.) at 30° for 2 hours. The translated reticulocyte lysate (at approximately 50,000–75,000 cpm) and 5 µl of each test serum was mixed in 10l0l of immunoprecipitation buffer( 20 mM Tris, pH 7.4, 150 mM NaCl and 1% Triton X-100). The reaction mixture was incubated overnight and 50 µl of 50% (v/v) protein A-agarose (Life Technologies, Gaithersburg, Md.) was added to the solution at 4° C. for one hour. After washing four times with immunoprecitate buffer, the immunoprecipitation nuxture was boiled in sample buffer and applied to an 8% SDS-PAGE gel. The gels were fixed with acetic acid/methanol (12.5%/12.5%) and then exposed to X-ray sensitive film overnight. The intensity of the IA-2 bands (approximately 106 KDa) was scored independently from 1–4+ by two independent investigators. One hundred coded sera comprising 50 from newly diagnosed patients and an equal number of matched controls were studied. Using this method, 66% of the patient sera but none of the controls were positive for autoantibodies to IA-2. Autoantibodies to $GAD_{65}$ were also performed by a D-ELISA method, and 52% were positive. In all, 86% of the patient sera but none of the controls were positive for autoantibodies to $GAD_{65}$ and/or IA-2, with 34% being positive to both antigens. There was an age-associated bias to the results. Of the patients diagnosed before age 20 years, 68% had IA-2 autoantibodies and 60% $GAD_{65}$ autoantibodies. However of the patients diagnosed after age 20 years, only 46% were positive for IA-2 autoantibodies while 86% were positive for $GAD_{65}$ autoantibodies. These results were greatly improved from the earlier study using ELISA assays and IA-2 fragments. There are several possible explanations. It is probable that the disease associated autoantibodies react to the antigen through conformational epitopes. Thus reactivity may be greatly enhanced using the whole protein rather than its fragments. The method also involves antibody reactivities with the IA-2 protein in its native undenatured state, conditions which enhance reactions to conformational epitopes. Such is also the case for autoantibody reactivities to $GAD_{65}$.

EXAMPLE 3

Evidence that IA-2 and $GAD_65$ are Antigens that are Components of the ICA Reaction There was an excellent correlation between occurrence of autoantibodies either to IA-2 or $GAD_{65}$ and ICA, in that only one of 15 ICA positive sera that did not react to $GAD_{65}$ was not positive for IA-2 autoantibodies. This suggested that $GAD_{65}$ and IA-2 are component antigens of the ICA response. This conclusion is proven by an experiment in which 6 sera were selected because they were positive for ICA, and only $GAD_{65}$ (n=2) or only IA-2 (n=4) and subjected to absorption studies. Recombinant baculomviral expressed human $GAD_{65}$ was used to absorb out the corresponding autoantibody before the sera were applied to the ICA reaction. We found that this procedure reduced the ICA reactivity only of the sera which were found to be positive for $GAD_{65}$ autoantibodies, as expected from Atkinson, et al.

(*J Clin Invest.* 91:350–356, 1993). Conversely, we also absorbed out the 6 sera after passage through an affinity column with glutathione sepharose beads to remove recombinant intracellular domain IA-2 expressed as a fusion protein with GST, before applying them to pancreatic sections for the ICA reaction, and found only those with autoantibodies to IA-2 to be reduced.

TABLE II

Absorption of ICA-Containing Sera with rIA-2 and $rGAD_{65}$

| Patient Serum | Reactivity of Sera With | | | Absorption of ICA-Containing Sera With | |
|---|---|---|---|---|---|
| | | | | rIA-2 | $rGAD_{65}$ |
| | | | | Reactivity of Absorbed Sera with | |
| | Islet Cells | rIA-2 | $rGAD_{65}$ | Islet Cells | |
| 1 | Pos | Pos | Neg | ↓↓ | — |
| 2 | Pos | Pos | Neg | ↓↓ | — |
| 3 | Pos | Pos | Neg | ↓ | — |
| 4 | Pos | Pos | Neg | ⊥ | ⊥ |
| 5 | Pos | Neg | Pos | — | ↓↓ |
| 6 | Pos | Neg | Pos | — | ↓↓ |

Reactivity of ICA-containing sera with islet cells as measured by intensity of immunofluorescence: greatly reduced (↓↓); reduced (↓); slightly reduced (⊥); no change (—).

These experiments document that $GAD_{65}$ and IA-2 are both antigens involved in the ICA response, however double absorptions with both antigens did not ablate any of the ICA responses, suggesting that autoantibodies to additional autoantigen(s) must be often present in ICA positive sera. A candidate antigen is IA-2 γ. Preliminary data suggests that more than 45% of sera from patients with IDD are autoantibody positive, compared to none of normal controls.

EXAMPLE 4

Evidence that Autoantibodies to IA-2 are Useful to Predict IDD

The human leukocyte antigens HLA-DR/DQ have been analyzed by a novel PCR based molecular typing system in more than 50 subjects with IDD. The high risk DRB1*03/DQB1*0201 and DRB1*04/DQB1*0302 haplotypes were over-represented in those positive for either autoantibodies to $GAD_{65}$ and/or IA-2. Thus, risk for IDD among patients and their relatives indicated a strong association between the IDD associated high risk HLA and appearance of these autoantibodies suggesting that the autoantibodies themselves would be expected to be associated with a high risk for IDD also.

In studies with 2500 normal school children and a similar number of first degree relatives of patients with IDD, we found that testing autoantibodies to IA-2, $GAD_{65}$, IAA and ICA, the combined predictive power of the IA-2 and $GAD_{65}$ test was greater than 90% in both groups for subsequent development of IDD.

EXAMPLE 5

Therapeutic Regimens

From the foregoing disclosure and experimental results it is evident that IA-2, an islet cell transmembrane tyrosine phosphatase of 105,847 KDa, is a major antigen in the pathogenesis of IDD, and is thus valuable in the diagnosis and therapy of the disease. Autoantibodies to the protein are useful in disease prediction both in non-diabetic relatives of patients affected by IDD, as well as in the general population. Such autoantibodies react mainly to determinants on the intracellular domain of IA-2. Such antibodies will be detectable by radioimmunoassay using recombinant IA-2, depletion or D-ELISA and/or by ELISA or immunoprecipitation as outlined here. Based upon experience of the inventors with $GAD_{65}$ and insulin autoantibody analyses, baculoviral based eukaryotic expression systems are likely to be preferred to fold the protein appropriately, and glycosylate the protein if this enhances the antibody binding ability. However, such expression systems as COS cells, yeast cells, and bacterial cells such as E. coli could be used for this purpose as those skilled in the art are readily able to appreciate.

Fluid-based immunoassays using the antigens and antibodies of this invention provide the greatest sensitivity to the method since autoantibodies of relevance mostly react to their respective autoantigen through conformational rather than through linear epitopes. The RIA and D-ELISA methods are most useful in filling these properties. Accordingly, autoantibodies to human $GAD_{65}$ and IA-2 antigens can replace the ICA method for prediction of IDD, with chemically based assays giving greater precision, reproducibility, and specificity without compromising sensitivity or positive predictive power.

Cellular responses, such as by proliferation or by cytoldne elaboration after in vitro exposure to IA-2, are also useful in disease prediction.

The IA-2 molecule or peptide derivatives of IA-2 are used in antigen based therapies, including giving the antigens intravenously to induce anergy, deliberately immunizing against the antigen such as to induce an antibody response mediated by T helper-2 type lymphocytes to induce immunosuppressive effects on the pathogenic T helper-1 lymphocyte subset; or orally fed antigen such as to induce anergy and suppressive effects. Intravenous $GAD_{65}$ antigens have been given in early life in NOD mice and shown to induce reductions in the degree of the inflammatory infiltrates or insulitis lesions and prevent the onset of hyperglycemia (Kauffman et al. Nature 1994:366:69–72). Subcutaneous immunizations by insulin and insulin B chains in incomplete Freunds adjuvant will prevent diabetes in NOD mice for prolonged periods without reductions in the insulitis lesions. The infiltrating cells however change their phenotype from ones that make large amounts of interferon gamma to ones that do not. Transfer of splenic lymphocytes from mice protected from diabetes in this way also convey protection for periods of up to a month. The intervention thus induces an active immunosuppressive effect and an insulitis lesion that is protective rather than destructive associated with a switch from Th1 to Th2 responses. Further, the effect must be beyond that merely involving autoimmunity to insulin, since beta cell destruction is arrested. The release of protective cytolines into the milieux of the islet must then also inhibit adjacent autoimmunity responses to other self-antigens through a bystander effect (Muir, Maclaren et al. J Clin Invest 1995:95: 628–634; Ramiya, Muir and Maclaren, Chin immunotherapy 1995:3:177–183.) Repeated feedings of defined autoantigens may also be used to inhibit ongoing autoimmune diseases. In the case of the NOD mice, this has occurred through orally administered insulin (Weiner et al. Natl Acad Sci USA 1991:88:10252–10256) as well as through the use of oral feedings of insulin and GAD (Muir, Maclaren et al. Diabetes/Metabolism Reviews 1994:9: 279–287). Accordingly, therapeutic methods employing IA-2 alone or in combination with other antigens improves the therapeutic efficacy of such treatments by providing an additional component of the ICA reaction.

EXAMPLE 6

Collection of Biological Fluid for Detection of IA-2 Autoantibodies

A volume of greater than 500 microliters of whole blood is collected from the individual to be tested for IA-2 autoantibodies. The blood is drawn into a glass vacutainer tube directly, or into a syringe followed by transfer into a glass vacutainer tube. In order to obtain sera (blood devoid of clotting factors), the common vacutainer tubes used are termed a red top tube (devoid of sodium heparin), or a serum separator (STS) tube. If a common red top tube is used, the tube is allowed to clot (a period of greater than 10 minutes), and the clot removed. At this period of time, either sample tube may be centrifuged for 5 minutes at 1000 rpm at room temperature. The serum within the sample is removed and placed into a plastic storage vial and sealed tightly. The sample can be frozen at $-20°$ until IA-2 autoantibody analysis.

EXAMPLE 7

Methods of Detecting IA-2 Antibodies

In addition to the use of immunoprecipitation techniques, the subject invention can be practiced utiliing any other procedures which facilitate detecting the presence of antibodies to IA-2. For example, other immunological methods which can be used include enzyme linked immunosorbent assay (ELISA) and radioimmunoassay (RIA). The principles and experimental methods of these procedures are well known to those skilled in the art. The assays can be carried out rapidly and efficiently by the use of natural or recombinant proteins which bind with the antibodies to IA-2. Both whole cell and cell lysate procedures are familiar to those working in this field and can be readily employed to detect the IA-2 antibodies.

The amino acid sequence of IA-2 can be analyzed to ascertain immunologically reactive epitopes. These epitopes are amino acid sequences which will react immunologically with the antibodies to IA-2. These sequences can then be produced recombinantly. For recombinant production, the DNA coding for the epitopes is inserted into a vector which is then used to transform an appropriate host cell to express the desired amino acid sequence. Although bacteria, insects, yeasts, and mammalian cells could all serve as appropriate hosts, if protein folding is an important factor in the reactivity of the epitope, then an eukaxyotic cell would be a preferred host.

Purified protein or lysate of the cells producing the protein could be used for the assays.

Also, an alternative to using IA-2 antigen would be to use antibodies generated to IA-2, otherwise known as an anti-antibody. This antibody would immunoprecipitate with IA-2, and the detection could be carried out as described above.

EXAMPLE 8

Treatment of IDD

The specific event or agent which triggers the onset of diabetes has not been identified. A virus carrying an antigen similar to the IA-2 protein may provoke both a normal immune response to the virus and also an abnormal, autoimmune response to IA-2 through it's molecular mimicry with the virus. The genetic susceptibility is thus expressed by an exaggerated or prolonged immune response to the environmental agent which initiates the disease process. It is also possible that the IA-2 protein may have a delayed expression in the development of islet cells in ontogeny, rendering it antigenic because tolerance to it would not have been developed in the early stages of life.

A novel therapy of the subject invention involves the injection into the bloodstream of a toxin bound to a purified form of the IA-2 antigen. The antigen-toxin complex would quickly reach the lymph nodes where it is taken up by immune cells that normally produce the antibodies to IA-2. Also, the antigen-toxin complex would be bound by the T-lymphocytes that recognize the IA-2 antigens on β-cells. Thus, the specific immune cells involved in β-cell destruction are poisoned and inactivated, leaving non-destructive immune cells unharmed. The hybrid protein could comprise, for example, a diphtheria toxin joined together with the IA-2 antigen. The construction of such a hybrid toxin could proceed, for example, according to the disclosure of U.S. Pat. No. 4,675,382 (Murphy) relating to hybrid proteins.

In a preferred method of the subject invention, prevention or treatment involves the administration of autoantigens to the susceptible individual. IDD has an autoimmune etiopathogenesis, as discussed above. Various mechanisms have been proposed that would account for the beneficial value of administering autoantigens as a preventive treatment. In addition, it is also well known in the art that the administration of autoantigens can be used to induce immunological non-responsiveness, that is, specific tolerance of the antigen. See U.S. Pat. No. 5,114,844; Nagler-Anderson et al. (1986) *Proc. Natl. Acad. Sci USA* 83:7443–7446; Miller et al. (1984) *Clin. Immunol. Immunopathol.* 31:231–240; Silverman et al. (1983) *J. Immunol.* 131:2651–2661; Michael (1989) *Immune Invest* 18:1049–1054. The administration of the IA-2 antigens according to the subject invention can be done using procedures, formulations, and administration routes well known in the art. As one skilled in the art having the benefit of this disclosure would appreciate, the administration of the IA-2 protein or peptide can be by, for example, parenteral, oral, intranasal, or by modification of the patient's genome to express an antigenic epitope.

EXAMPLE 9

Use of IA-2 Antibodies in Conjunction with Pancreas Transplantation

One approach for treatment of a patient with IDD is to transplant normal islets as replacements for the damaged or destroyed β-cells. Segmental and whole pancreas transplantations have been performed successfully in a number of patients with diabetes. However, permanent immunosuppressive therapy is required to maintain the grafts and prevent rejection Segmental or whole pancreas transplants under continuous immunosuppressive therapy have produced normal levels of blood glucose in some patients with diabetes. Pancreatic transplants are done late in the course of diabetes and will probably not reverse complications such as nephropathy and indeed may worsen retinopathy.

Importantly, successful pancreatic grafts between identical twins have been maintained without immunosuppressors; however, autoimmune islet cell destruction has occurred with recurrence of diabetes. Thus, even when the graft is not rejected, there is obligatory need for immunotherapies to prevent disease recurrence. The destruction (rejection) of transplanted islets may be due, at least in part, to the representation of autoantigens responsible for the autoimmune destruction. There is no specific immunotherapy to prevent the autoimmune destruction (rejection of transplanted islets/pancreas) at present. In order to prevent the autoimmune destruction of either transplanted islet cells or pancreas, a specific immunotherapy using a hybrid toxin, as detailed above, can be used to prevent islet cell destruction. The combined use of the immunotherapies could make islet cellpancreas transplantation a therapeutic tool for the treatment of IDD.

EXAMPLE 10

Kits for Assay of IA-2 Autoantibodies and IDD

A reagent kit can be provided which facilitates convenient analysis of serum samples using the novel procedures described here. Kits can be prepared which utilize recombinant or synthetically produced intact IA-2 protein(s) or immunoreactive peptides to serve as an antigen for the detection of antibodies to IA-2. Alternatively, antibodies specifically developed to detect antibodies to IA-2 may also be useful. The principles and methods for ELISA and RIA technologies to detect antibodies are well-established.

As an example, for the ELISA assay, one such kit could comprise the following components:

1. IA-2 protein, peptide, or antibodies to IA-2 antibodies;
2. Enzyme (e.g., peroxidase);
3. Conjugated animal anti-human immunoglobulin; and
4. Positive and negative controls.

The above kit could be modified to include 96 well plastic plates, colorimetric reagents, ELISA readers, blocking reagents, and wash buffers Inclusion of $GAD_{65}$ antigen would also be highly preferred.

Also by way of example, for the RLA, one such kit could comprise the following components:

1. Radiolabeled IA-2 protein(s), peptide, or antibodies to IA-2 antibodies;
2. Wash buffers;
3. Polyethylene glycol;
4. Goat or sheep antihuman precipitating (second) antibodies; and
5. Positive and negative controls.

Either of the above kits may be modified to include any appropriate laboratory supplies or to exclude non-essential compounds. Presence of IA-2 autoantibodies as detected by using this kit is indicative of IDD or susceptibility to IDD, especially if in addition, $GAD_{65}$ reactive autoantibodies are detected.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for detecting insulin dependent diabetes or susceptibility to developing insulin dependent (type 1) diabetes in a patient, which comprises contacting an antibody-containing patient sample with a combination of IA-2 and $GAD_{65}$, and detecting the presence of antibodies in the serum of said patient which bind to a combination of IA-2 and $GAD_{65}$, wherein the presence of said antibodies is indicative of the presence of immune mediated (type 1) diabetes or the susceptibility to developing immune mediated (type 1) diabetes in said patient compared to patients lacking antibodies that bind to IA-2 and $GAD_{65}$.

2. The method of claim 1 which is a radioimmunoassay, an ELISA assay, a depletion ELISA, or an immunoprecipitation method.

3. The method of claim 2 in which recombinant IA-2 is used.

4. The method of claim 3 in which the recombinant IA-2 is produced in a baculovirus expression system.

5. A composition comprising both an isolated $GAD_{65}$ and an isolated IA-2 molecule.

6. A kit for detection of autoantibodies associated with diabetes which comprises IA-2 protein or the intracellular domain of the IA-2 protein and wherein said kit further comprises $GAD_{65}$ protein, antigenic peptides thereof, or antibodies to $GAD_{65}$.

7. The kit of claim 6 which further comprises labeled animal anti-human immunoglobulin.

8. The kit of claim 6 which further comprises a microtiter plate.

9. The kit of claim 6 which further comprises colorimetric agents, ELISA blocking reagents, positive and negative controls, or wash buffers.

10. The kit of claim 6 in which the IA-2 protein or the intracellular domain of the IA-2 protein is radiolabeled or conjugated to a marker molecule.

11. The kit of claim 6, wherein the intracellular domain consists of amino acid residues 603–979, of IA-2.

* * * * *